(12) United States Patent
Pressman et al.

(10) Patent No.: US 7,045,666 B2
(45) Date of Patent: May 16, 2006

(54) BROMINATION OF HYDROXYAROMATIC COMPOUNDS AND FURTHER CONVERSION TO DIHYDROXYAROMATIC COMPOUNDS

(75) Inventors: Eric James Pressman, East Greenbush, NY (US); John Yaw Ofori, Niskayuna, NY (US); Grigorii Lev Soloveichik, Latham, NY (US); Ryan Christopher Mills, Clifton Park, NY (US); Jonathan Lloyd Male, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/342,475

(22) Filed: Jan. 16, 2003

(65) Prior Publication Data

US 2004/0143144 A1     Jul. 22, 2004

(51) Int. Cl.
*C07C 39/24* (2006.01)
(52) U.S. Cl. ...................................... 568/779
(58) Field of Classification Search ................ 568/779
See application file for complete search history.

(56) References Cited

U.S. PATENT DOCUMENTS

| | | | | |
|---|---|---|---|---|
| 1,934,656 A | | 11/1933 | Britton et al. | |
| 3,796,732 A | * | 3/1974 | Brenner | 552/310 |
| 3,933,681 A | * | 1/1976 | Hutchings et al. | 502/24 |
| 3,987,068 A | * | 10/1976 | Reilly | 552/296 |
| 5,177,258 A | | 1/1993 | Becker et al. | |
| 6,693,221 B1 | * | 2/2004 | Mills et al. | 568/779 |
| 6,815,565 B1 | * | 11/2004 | Mills et al. | 568/779 |

* cited by examiner

*Primary Examiner*—Michael L. Shippen
(74) *Attorney, Agent, or Firm*—Andrew J. Caruso; William E. Powell, III

(57) ABSTRACT

Brominated hydroxyaromatic compounds such as p-bromophenol are prepared by contacting a hydroxyaromatic compound with oxygen and a bromine source such as hydrogen bromide or an alkali metal or alkaline earth metal bromide in an acidic medium, in the presence of elemental copper or a copper compound as catalyst. The brominated product of this reaction may be converted alternately to a dihydroxyaromatic compound such as hydroquinone by hydrolyses, or a dihydroxybiphenyl compound such as 4,4'-dihydroxybiphenyl by reductive coupling.

19 Claims, 1 Drawing Sheet

BROMINATION OF HYDROXYAROMATIC COMPOUNDS AND FURTHER CONVERSION TO DIHYDROXYAROMATIC COMPOUNDS

BACKGROUND OF THE INVENTION

This invention relates to the reactions of hydroxyaromatic compounds, and more particularly to the conversion of such compounds to brominated derivatives, monocyclic dihydroxyaromatic compounds and dihydroxybiphenyls.

Monocyclic dihydroxyaromatic compounds such as hydroquinone and dihydroxybiphenyls such as 4,4'-dihydroxybiphenyl (hereinafter sometimes simply "biphenol") have numerous uses in the chemical industry. For example, both compounds can be used in polymer preparation, notably in the preparation of polycarbonates, polysulfones and polyimides, especially polyetherimides.

There are various methods for the preparation of hydroquinone and biphenol. As examples of such methods, each compound can be prepared from p-bromophenol, hydroquinone by hydrolysis and biphenol by reductive coupling in the presence of a noble metal catalyst, a base and a reducing agent.

Brominated hydroxyaromatic compounds, as exemplified by p-bromophenol, can be prepared by reaction of the precursor hydroxyaromatic compound with elemental bromine or with various kinds of bromides. For the most part, the use of hydrogen bromide alone is not successful. Auxiliary reagents are required; these may include oxidizing agents, reducing agents, catalysts and/or complexing agents. As a result, the commercial production of bromophenols by reaction of phenols with hydrogen bromide or other simple ionic bromides has, in general, not been pursued.

Normally, chemical plants are set up to produce a single product or group of products in a single reaction or a unitary sequence of reactions. It is thus possible to set up a single set of equipment and use it, on either a batch or continuous basis, permanently to produce the desired product.

Toll producers of chemicals, on the other hand, may utilize a wide variety of equipment, choosing individual items for use depending on the chemical then being produced. To vary the product, they may vary the reactors employed and/or the connections between reactors so as to design a suitable set of equipment for the particular product.

So far as is presently known, the use of a unitary set of equipment to produce two or more widely diverse products is not a commercial alternative.

SUMMARY OF THE INVENTION

The present invention provides a facile method for the preparation of brominated hydroxyaromatic compounds using simple ionic bromides such as hydrobromic acid. Also provided is a method and apparatus for converting the brominated products thus prepared into two separate and diverse classes of chemicals, on an alternating basis. Thus, a first product may be synthesized as needed, after which a second product may be synthesized without any change in the equipment employed.

In a first aspect, the invention is a method for preparing a brominated hydroxyaromatic compound which comprises contacting a hydroxyaromatic compound with oxygen and a bromide source in an acidic medium, in the presence of elemental copper or a copper compound as catalyst.

A second aspect of the invention is a method for converting a hydroxyaromatic compound to useful products which comprises:

(A) brominating said hydroxyaromatic compound to a p-brominated product in a first reaction vessel, and (B) transferring said p-brominated product to a second reaction vessel and alternately (1) hydrolyzing it to form a p-dihydroxyaromatic compound and (2) reductively coupling it to form a dihydroxybiphenyl compound.

A third aspect is apparatus for conducting chemical reactions, said apparatus comprising:

I. a first reaction vessel adapted for the bromination of a hydroxyaromatic compound to a p-brominated product, and II. a second reaction vessel communicating directly or indirectly with said first vessel, said second vessel adapted for the alternate hydrolysis of said p-brominated product to a dihydroxyaromatic compound and reductive coupling of said p-brominated product to a dihydroxybiphenyl compound.

BRIEF DESCRIPTION OF THE DRAWING

The drawing is a block diagram of the apparatus of the invention.

DETAILED DESCRIPTION; PREFERRED EMBODIMENTS

Figure 1:
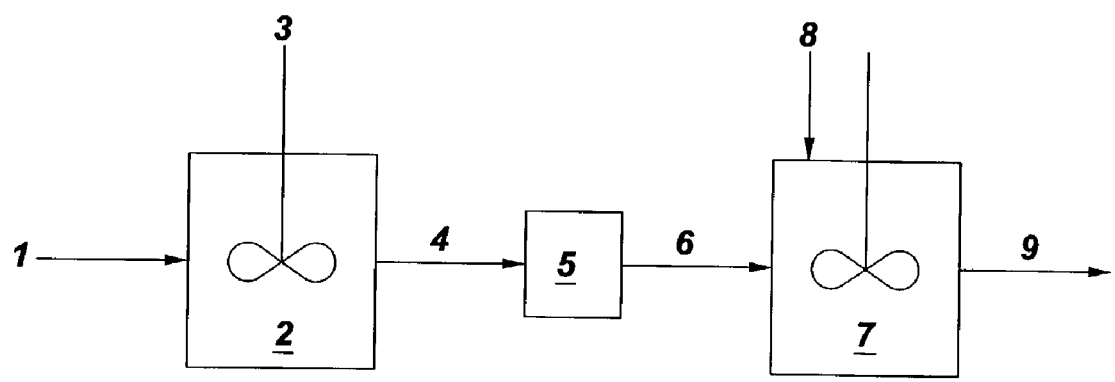

The common initial reactant for all products obtained according to this invention is a hydroxyaromatic compound, preferably a monocyclic monohydroxyaromatic compound. It may be an unsubstituted hydroxyaromatic compound such as phenol, or a substituted compound provided, however, that the 4-position is unsubstituted and thus available for bromination. Preferred substituents (one or more) are alkyl groups, particularly $C_{1-4}$ alkyl. Illustrative compounds are those having the formula

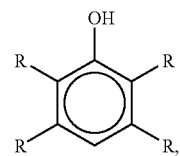

wherein each R is independently hydrogen or a substituent, preferably $C_{1-4}$ alkyl.

Particularly preferred in most instances is phenol, and specific reference will be frequently made to phenol hereinafter. However, homologous compounds such as o- and m-cresol may be substituted for phenol as desired.

According to the first aspect of the invention, the phenol is contacted with oxygen and a bromine compound. The oxygen is employed in stoichiometric excess and may be pure oxygen or may be employed in the form of air or oxygen-enriched air; ordinary air is often preferred. Contact may be with flowing oxygen or air or under pressure, typically up to about 100 atm.

Suitable bromine compounds include hydrogen bromide and bromide salts. Hydrogen bromide may be employed in any form; examples are gaseous HBr, aqueous HBr (hydrobromic acid) and HBr in solution in a polar organic solvent, typically one of the solvents described hereinafter. Bromide salts include alkali metal bromides such as sodium bromide and potassium bromide and alkaline earth metal bromides such as calcium bromide and magnesium bromide. Hydrobromic acid is generally the preferred bromine compound. It may be employed at any concentration, including the commercially available 48% (by volume) aqueous solution.

Said contact is in an acidic medium. Aqueous acidic media including Brønsted acids generally, and particularly including sulfuric acid, phosphoric acid and nitric acid, may be employed; or, if hydrobromic acid is the bromine compound employed, it may serve as the acidic medium. Polar organic solvents may also be present. These may include polar aprotic solvents such as acetonitrile, dimethyl sulfoxide, chloroform and o-dichlorobenzene, as well as protic solvents such as water, acetic acid and excess hydroxyaromatic compound. Acetic acid and acetonitrile are frequently preferred. Mixtures of the foregoing solvents may be employed. It is often preferred that the reaction medium be anhydrous.

Said contact is also in the presence of elemental copper or a copper compound as a catalyst of the bromination reaction. Copper compounds are generally preferred. Examples are cupric sulfate, cupric chloride, cupric bromide, cuprous chloride and cuprous bromide. Cupric bromide is often preferred by reason of its relatively low cost and particular suitability, as contact with hydrobromic acid will usually convert other cupric salts to the bromide.

The bromination reaction may be conducted at a temperature in the range of about 20–150° C., preferably about 60–80° C. Proportions of copper source are most often in the range of about 0.1–30 mole percent of copper based on hydroxyaromatic compound. The molar ratio of ionic bromide to hydroxyaromatic compound is preferably less than 1:1, to minimize conversion to dibromo and more highly brominated compounds; ratios in the range of about 0.2–0.9:1 are typical.

The product of the bromination reaction is usually predominantly the p-bromo compound, with minor amounts of o-bromo compound and dibromo and higher compounds also being present. Conversion of phenol to bromophenols is, for the most part, at least 40%, "conversion" being defined as total phenol (in weight units or moles) consumed as a percentage of phenol originally present. Selectivity to 4-bromophenol is usually at least 80% and often greater than 90%, "selectivity" meaning moles of the specific product formed as a percentage of moles of phenol consumed.

Separation of the bromophenol compounds prepared according to the invention may be effected by art-recognized methods. Distillation is generally preferred, since there is a difference of more than 40° C. between the boiling points of 2-bromophenol (194.5° C.) and 4-bromophenol (238° C.) and the dibromophenols have even higher boiling points. Distillation may be conducted under reduced pressure to minimize thermal decomposition.

According to the second aspect of the invention, a bromination reaction, which may preferably be but need not be the reaction of the first aspect, is conducted in a first reaction vessel, which may be a conventional tank reactor as used in a batch process or a continuous stirred tank reactor (CSTR) as used in a continuous process. When necessary or appropriate, the bromination product mixture may be transferred from said first vessel to appropriate separation means. The p-brominated product is thence transferred to a second reaction vessel, which may also be a tank reactor or CSTR, for performance of the second step.

The key feature of this aspect is the performance alternately of the hydrolysis and reductive coupling steps. These are alternated as desired to produce the currently desired product; by "alternately" is meant that the hydrolysis and reductive coupling operations are performed in succession as required by product necessities, with switching between the two operations when needed. Both the hydrolysis and the reductive coupling steps may be performed batchwise or continuously, as described hereinabove for the bromination step.

For hydrolysis to a dihydroxyaromatic compound such as hydroquinone (aspect B-1), the bromophenol is contacted with an aqueous base in the presence of a suitable catalyst, typically elemental copper or an oxide thereof, at a temperature of at least about 75° C. and preferably in the range of about 75–150° C. Illustrative conditions are those described in any part of U.S. Pat. No. 1,934,656, the disclosure of which is incorporated by reference herein.

For reductive coupling to a dihydroxybiphenyl compound such as biphenol (aspect B-2), the bromophenol is contacted with a reducing agent such as formic hydrazide in the presence of an aqueous base and a platinum group catalyst, preferably palladium which may be supported on carbon. This reaction may be carried out at temperatures similar to those of the hydrolysis step, typically in the range of about 60–100° C. U.S. Pat. No. 5,177,258 is incorporated by reference herein for its disclosure of typical conditions for the reductive coupling reaction.

A notable feature of reactions B-1 and B-2 is the similarity of the conditions under which they are performed. Both require relatively low temperatures, no higher in general than about 150° C. Both employ aqueous base, most often an alkali metal hydroxide and a metal-containing catalyst. Both can be conducted in either a glass or a metal reaction vessel; if a vessel comprising copper is used for hydrolysis, it may provide enough of that metal to serve as a catalyst.

Thus, it is possible to use the second vessel for either hydrolysis or reductive coupling, with little or no alteration other than cleaning before changing from one reaction to the other. This has the advantage of making it possible to conduct the hydrolysis and reductive coupling reactions on an alternating basis.

Reference is now made to the drawing to help explain the apparatus of the invention. Phenol, hydrobromic acid, copper compound and any solvent employed are introduced at 1 into first reaction vessel 2, which may be a tank reactor, a CSTR, a plug flow reactor or the like. The reactants may be introduced through separate lines or premixed and introduced through a single line.

In vessel 2, the reactants are brought into contact and mixed with the aid of agitator 3, under conditions for preparation of bromophenols. When the reaction has reached substantial completion, the product is withdrawn at 4 and passed into optional separation (e.g., distillation) means 5, where the constituents of the product are separated and the desired constituent, usually 4-bromophenol, is passed at 6 into second reaction vessel 7 which is equipped with agitator 10.

Depending on the product desired, the constituent introduced at 6 may be contacted at 8 with aqueous base and a copper-containing catalyst under conditions for hydrolysis of bromophenol to hydroquinone, which is removed at 9. When the need for production of hydroquinone has been met, vessel 7 may be cleaned and introduction of constituent at 6 resumed, while reducing agent, aqueous base and platinum group catalyst are introduced at 8. Conditions are established for the reductive coupling of bromophenol to biphenol and its removal at 9. Other equipment suitable for purification of hydroquinone or biphenol may be fed at 9 from vessel 7.

The invention is illustrated by the following examples. All percentages are by weight.

EXAMPLE 1

To a 3-dram vial were charged 1.37 ml (15.56 mmol) of phenol, 0.112 g (0.5 mmol) of cupric bromide, 1.39 ml (12.50 mmol) of 48% hydrobromic acid and 2.20 ml of acetonitrile. The vial was sealed with a cap containing a hole to allow for air flow during the reaction and placed in an aluminum block. The block was placed in a 450-ml autoclave reactor, pressurized to 34.0 atm with air and heated at 65° C. for 1 hour. It was then cooled to room temperature and depressurized. The resulting mixture was analyzed by vapor phase chromatographic analysis and shown to contain 7.39% phenol, 28.63% 4-bromophenol, 5.59% 2-bromophenol and 0.68% 2,4-dibromophenol, corresponding to 72% phenol conversion, with 82% 4-bromophenol selectivity and a total monobromophenol selectivity of 98%.

EXAMPLE 2

To a 3-dram vial were charged 1.59 ml (15.39 mmol) of o-cresol, 0.112 g (0.5 mmol) of cupric bromide, 1.48 ml (12.47 mmol) of 48% hydrobromic acid and 1.92 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 13.23% o-cresol, 27.74% 4-bromo-2-methylphenol and 0.93% 6-bromo-2-methylphenol, corresponding to 56% o-cresol conversion, with 96% 4-bromo-2-methylphenol selectivity and a total monobromophenol selectivity of 99%.

EXAMPLE 3

To a 3-dram vial were charged 1.37 ml (15.56 mmol) of phenol, 0.112 g (0.5 mmol) of cupric bromide, 1.30 ml (6.85 mmol) of a 30% solution of hydrogen bromide in acetic acid and 2.31 ml of acetonitrile. The vial was sealed and located as in Example 1, pressurized to 34.0 atm with air and heated at 65° C. for 1 hour. It was then cooled to room temperature and depressurized. The resulting mixture was analyzed by vapor phase chromatographic analysis and shown to contain 14.12% phenol, 19.15% 4-bromophenol and 1.15% 2-bromophenol, corresponding to 44% phenol conversion, with 96% 4-bromophenol selectivity and a total monobromophenol selectivity of 100%.

EXAMPLE 4

An apparatus as shown in the drawing is employed, with each of vessels 2 and 7 being a tank reactor. In vessel 2, the procedure of Example 3 is performed in amounts suitable for commercial production on reagents introduced separately at 1. The product is withdrawn at 4 and distilled in distillation apparatus 5. The 4-bromophenol recovered by distillation is passed at 6 into vessel 7 fabricated of copper.

In a first run, aqueous sodium hydroxide solution is introduced at 8 and the conditions described in Example 1 of U.S. Pat. No. 1,934,656 are maintained. The hydroquinone obtained as product is worked up and isolated as in that example.

EXAMPLE 5

In a second run following the preparation and isolation of 4-bromophenol as in Example 4, a coupling reaction to produce biphenol is performed in accordance with the general disclosure of U.S. Pat. No. 5,177,258. The reaction employs 1 part of 4-bromophenol in vessel 7 and 2.5 parts of sodium hydroxide, 0.6 part of palladium catalyst (5% by weight on carbon) and 3 parts of formic hydrazide in water, introduced at 8.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a brominated hydroxyaromatic compound which comprises contacting a hydroxyaromatic compound with oxygen and a bromine compound selected from the group consisting of hydrogen bromide and ionic bromide salts in an acidic medium, in the presence of elemental copper or a copper compound as catalyst.

2. A method according to claim 1 wherein said medium is anhydrous.

3. A method according to claim 1 wherein the hydroxyaromatic compound has the formula

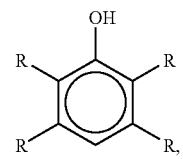

wherein each R is independently hydrogen or $C_{1-4}$ alkyl.

4. A method according to claim 1 wherein the hydroxyaromatic compound is phenol, o-cresol or m-cresol.

5. A method according to claim 4 wherein the hydroxyaromatic compound is phenol.

6. A method according to claim 4 wherein the hydroxyaromatic compound is o-cresol.

7. A method according to claim 1 wherein the bromine compound is hydrogen bromide.

8. A method according to claim 1 wherein the oxygen is provided by air.

9. A method according to claim 1 wherein the copper is provided as cupric bromide, cupric sulfate, cupric chloride, cuprous chloride or cuprous bromide.

10. A method according to claim 9 wherein the copper is provided as cupric bromide.

11. A method according to claim 1 wherein flowing oxygen is employed.

12. A method according to claim 1 wherein oxygen under pressure is employed.

13. A method according to claim 1 wherein a polar organic solvent is also present.

14. A method according to claim 1 wherein the solvent is acetonitrile, dimethyl sulfoxide, chloroform, o-dichlorobenzene, water, phenol, o-cresol, m-cresol, propionic acid or acetic acid.

15. A method according to claim 14 wherein the solvent is acetonitrile or acetic acid.

16. A method according to claim 1 wherein a temperature in the range of about 20–150° C. is employed.

17. A method according to claim 1 wherein a molar ratio of ionic bromide to hydroxyaromatic compound less than 1:1 is employed.

18. A method according to claim 1 wherein the proportion of copper source is in the range of about 0.1–30 mole percent of copper based on hydroxyaromatic compound.

19. A method for preparing 4-bromophenol, 4-bromo-o-cresol or 4-bromo-m-cresol which comprises contacting phenol, o-cresol or m-cresol with air and hydrogen bromide in an acidic medium, in the presence of cupric bromide.

\* \* \* \* \*